(12) United States Patent
Anderson et al.

(10) Patent No.: US 9,465,131 B2
(45) Date of Patent: Oct. 11, 2016

(54) METHODS FOR DETERMINING DIELECTRIC PERMITTIVITY SPECTRUM OF UNDERGROUND ROCK FORMATIONS

(71) Applicant: Schlumberger Technology Corporation, Sugar land, TX (US)

(72) Inventors: Barbara Anderson, Brookfield Center, CT (US); Thomas D. Barber, Houston, TX (US); Emmanuel Legendre, Sevres (FR); Martin G. Luling, Paris (FR); Pabitra Sen, Chapel Hill, NC (US); Reza Taherian, Al-Khobar (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/510,058

(22) Filed: Oct. 8, 2014

(65) Prior Publication Data

US 2015/0025807 A1 Jan. 22, 2015

Related U.S. Application Data

(63) Continuation of application No. 13/260,561, filed as application No. PCT/EP2010/001898 on Mar. 25, 2010, now Pat. No. 8,884,623.

(30) Foreign Application Priority Data

Apr. 2, 2009 (EP) ..................................... 09157159

(51) Int. Cl.
*G01V 3/18* (2006.01)
*E21B 47/00* (2012.01)
(Continued)

(52) U.S. Cl.
CPC .................. *G01V 3/18* (2013.01); *E21B 47/00* (2013.01); *G01N 27/00* (2013.01); *G01N 33/24* (2013.01); *G01V 3/30* (2013.01); *G01V 3/38* (2013.01)

(58) Field of Classification Search
CPC ............ G01V 3/00; G01V 3/30; G01V 3/38; G01V 3/18; G01V 3/28; G01V 3/20; G01V 3/22; G01V 3/24; G01V 3/26; G01V 11/00; G01N 27/00; G01N 33/24; E21B 47/00
See application file for complete search history.

(56) References Cited

U.S. PATENT DOCUMENTS 3,893,021 A * 7/1975 Meador ................... E21B 49/00
324/341
4,209,747 A * 6/1980 Huchital .................. G01V 3/30
324/338

(Continued)

*Primary Examiner* — Minh N Tang
*Assistant Examiner* — David Frederiksen
(74) *Attorney, Agent, or Firm* — Michael Dae

(57) ABSTRACT

Techniques involve determining the frequency-dependent dielectric permittivity spectrum of a rock sample. Determining the frequency-dependent dielectric permittivity may involve defining a series of electromagnetic measurement data having at least a measurement at a frequency from which a substantially frequency-independent value of dielectric permittivity $\in_\infty$ can be obtained. The electromagnetic measurement data also includes measurements at different frequencies from which values for frequency-dependent dielectric permittivity $\in_{rock}$ (f) can be obtained. Using these measurements, the frequency-dependent spectrum of the sample may be determined.

10 Claims, 3 Drawing Sheets

(51) Int. Cl.
    *G01N 27/00*  (2006.01)
    *G01N 33/24*  (2006.01)
    *G01V 3/30*   (2006.01)
    *G01V 3/38*   (2006.01)

(56) References Cited

U.S. PATENT DOCUMENTS

| | | | | |
|---|---|---|---|---|
| 4,652,828 A | * | 3/1987 | Kenyon | G01V 3/38 324/338 |
| 4,899,112 A | * | 2/1990 | Clark | G01V 3/30 324/338 |
| 5,345,179 A | * | 9/1994 | Habashy | G01V 3/30 324/338 |
| 6,100,696 A | * | 8/2000 | Sinclair | G01V 3/28 324/338 |
| 7,363,160 B2 | * | 4/2008 | Seleznev | G01V 3/30 702/13 |
| 7,376,514 B2 | * | 5/2008 | Habashy | G01V 3/30 702/13 |
| 2007/0090846 A1 | * | 4/2007 | Habashy | G01R 27/2647 324/600 |
| 2010/0283486 A1 | * | 11/2010 | Comparon | G01V 3/30 324/686 |
| 2012/0153958 A1 | | 6/2012 | Anderson et al. | |

\* cited by examiner

METHODS FOR DETERMINING DIELECTRIC PERMITTIVITY SPECTRUM OF UNDERGROUND ROCK FORMATIONS

TECHNICAL FIELD

This invention relates to methods for determining the dielectric permittivity spectrum of underground rock formations. In particular, the invention relates to methods for interpreting electromagnetic measurements of the types commonly made during logging of oil or gas wells or the like.

BACKGROUND ART

It has been known for some time that fluid-saturated rocks have dispersive electromagnetic properties, i.e. frequency-dependent dielectric permittivity and conductivity. Most electromagnetic measurements are designed to determine the electric conductivity of such rocks. Ampère-Maxwell's law states that the electric conductivity $\sigma$ and the relative dielectric permittivity $\in_r$ are intimately tied as real and imaginary parts of a complex-valued conductivity $\sigma^* = \sigma - i\omega\in_0\in_r$ with the circular frequency $\omega$. Frequently they are also represented as complex-valued permittivity $\in^*_r = \in_r + i(\sigma/\omega\in_0)$ with the conductivity scale defined as $\sigma_0 \equiv \omega\in_0$.

The electric conductivity and relative dielectric permittivity have different dispersive behaviour: the electric conductivity tends to increase slightly with frequency while the dielectric permittivity decreases strongly, this behaviour is schematically shown in FIG. 1. Extensive laboratory studies have shown that above about 600 MHz the square root of the complex dielectric permittivity of a rock is the volumetric average of the square root of the individual complex dielectric permittivities of the constituting material components. This empirical averaging rule is known as the "Complex Refractive Index Method" (CRIM).

The dispersion behaviour of the electromagnetic parameters of heterogeneous media has been studied throughout the twentieth century. Early work by Peter Debye in the 1920s was subsequently refined by Cole and Cole in the 1950s and others in the 1980s.

The later work clearly showed the dispersion of the dielectric permittivity. At the same time, some dielectric formation-evaluation tools were developed for the oilfield wireline logging industry, notably the EPT (Electromagnetic Propagation Tool) of Schlumberger, operating at 1.1 GHz where the dispersion is minimum. More recently, tools that would measure the dielectric permittivity at several frequencies from 100 MHz to 1 GHz have been developed. Such tools include array dielectric logging tools.

The Deep Propagation Tool, operating at 25 MHz was introduced in the 1970s to provide a dielectric measurement beyond the depth of investigation of the EPT. DPT dielectric measurements were found to be substantially different than those from the EPT, and the tool was not widely used because it was difficult to perform a consistent dielectric interpretation.

A number of techniques have been proposed which use dielectric measurements at different frequencies in the range $10^6$-$10^{10}$ Hz. Examples can be found in U.S. Pat. No. 5,059,907, U.S. Pat. No. 5,469,062, U.S. Pat. No. 7,376,514, GB2430264 and GB2430265.

This invention is based on the recognition that useful information about formation properties can be obtained from a range of dielectric measurements below $10^6$ Hz.

DISCLOSURE OF THE INVENTION

A first aspect of this invention provides a method for determining the frequency-dependent dielectric permittivity spectrum of a rock sample, comprising:
  defining a series of electromagnetic measurement data comprising at least a first measurement at a frequency from which a substantially frequency-independent value of dielectric permittivity $\in_\infty$ can be obtained; and at least second and third measurements at different frequencies from which values for frequency-dependent dielectric permittivity $\in_{rock}(f)$ can be obtained; and
  using the first, second and third measurements to determine the frequency-dependent spectrum of the sample.

The first measurement is typically made at a frequency of $10^8$ Hz or above, and the second and third measurements are typically made a frequencies of $10^7$ Hz or below.

The invention also broadly provides a method for determining the frequency-dependent dielectric permittivity spectrum of a rock sample, comprising:
  defining a series of electromagnetic measurement data comprising at least a first measurement at a frequency of $10^8$ Hz or above; and at least second and third measurements at different frequencies of $10^7$ Hz or below; and
  using the first, second and third measurements to determine the frequency-dependent spectrum of the sample.

Where the frequency-dependent part of the spectrum obeys the relationship $\in_{rock}(f) = \in_1(f) + \in_\infty$ wherein $\in_1(f)$ defines the frequency-dependent part of a measured value of dielectric permittivity, the method preferably comprises:
  determining the dc permittivity $\in_{dc}$;
  determining the characteristic frequency $f_0$, the lowest frequency for which the relationship $\log(\in_1(f)) = -\beta \log(1+f/f_0) + \log(\in_{dc})$ holds true; and determining the slope of the frequency dependent part of the spectrum between $f_0$ and the frequency $f_c$ at which the spectrum becomes substantially frequency independent.

Determining $\in_{dc}$ and $f_0$ can be achieved by providing measurements of $\in_{rock}(f)$ for at least two frequencies and applying a fitting routine to the relationship $\log(\in_{rock} - \in_\infty) = -\log(1+f/f_0) + \log(\in_{dc})$.

$f_c$ can be determined from the relationship $$f_c = f_0 \left(\frac{\varepsilon_{dc}}{\varepsilon_\infty}\right).$$

The slope is preferably the slope of the plot of $\log \in_1$ vs $\log(1+f/f_0)$. In this case, $f_c$ can also be determined from the plot.

The slope can be used to estimate the pore size distribution of the rock, and the value of $f_c$ can be used to estimate the salinity of the pore fluids in the rock.

The method can further comprise making a series of electromagnetic measurements in a borehole extending through the rock sample and using the measurement to define the data series. The first measurement can obtained in a separate operation from the second and third measurement, and the measurements can be a combination of different wireline and/or lwd measurements.

Further aspects of the invention will be apparent from the following description.

MODE(S) FOR CARRYING OUT THE INVENTION

Figure 1:
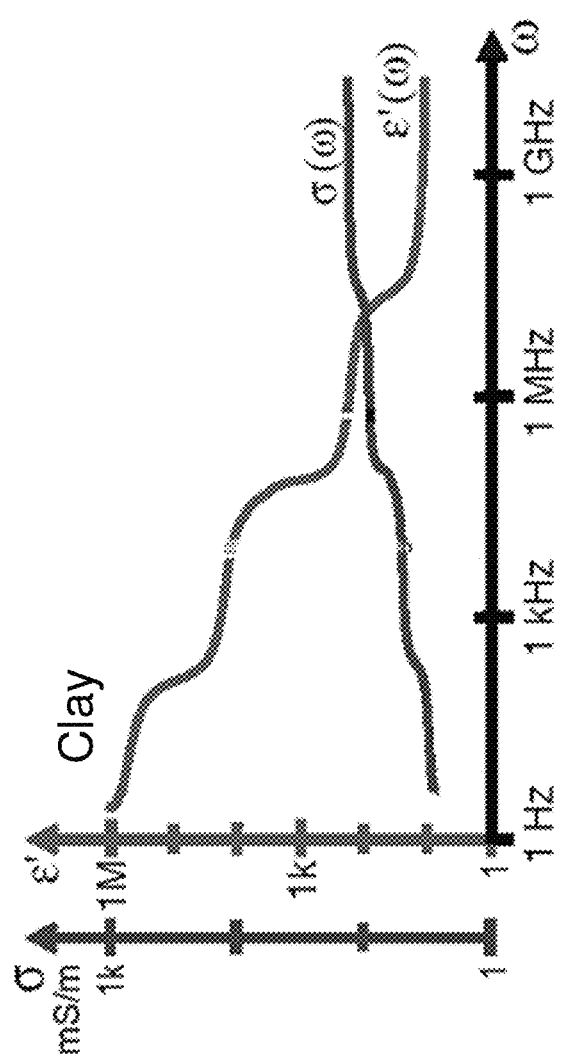
FIG. 1 shows a plot of permittivity and conductivity at different frequencies.

This invention is based on the identification of several distinct polarization processes at the microscopic grain structure or the even smaller molecular scale. These competing processes become active over distinct, but overlapping frequency ranges from the single-Hz through the kHz and low-MHz range up to the 100 MHz range. The term "dielectric spectroscopy" is used to refer to characterizing the frequency dependence which is the finger-print of the rock property.

With decreasing frequency several competing processes contribute to an ever-increasing relative dielectric permittivity. The availability of different tools with their widely varying operating frequencies allows measurement of the electromagnetic rock properties in a way that separates out the different microscopic processes. This multi-frequency measurement and the associated decoupling of the various processes shall be called dielectric spectroscopy.

This invention proposes the use of wireline and LWD resistivity and dielectric logging tools over a wide frequency range to determine the complex-valued rock conductivity $\sigma^* = \sigma - i\omega\epsilon_0\epsilon_r$, or its equivalent, $\epsilon^*_r = \epsilon_r + i(\sigma/\omega\epsilon_0)$. The frequency dependence of these quantities, especially of the relative dielectric permittivity $\epsilon_r$ is attributed to various microscopic polarization processes that are combined in a simple model that captures the frequency dependence with a limited number of parameters. This frequency-dependent polarization shall be called dielectric spectroscopy.

Ampère-Maxwell's equation couples the displacement current $\vec{D}$ and the galvanic current density $\vec{j}$ into one single quantity:

$$\vec{\Delta} \times \vec{H} = \partial_t \vec{D} + \vec{j} \quad (1)$$

A universal time dependence $\epsilon^{-i\omega t}$ replaces the time derivative $\partial_t$ by the multiplicative factor $\delta_t \to -i\omega$. The constitutive relationships between the electric field $\vec{E}$ and the displacement and galvanic current densities introduce and combine the dielectric permittivity $\epsilon = \epsilon_0 \epsilon_r$ and the electric conductivity $\sigma$ into the complex-valued conductivity $\sigma^* = \sigma - i\omega\epsilon_0\epsilon_r$. Ampère-Maxwell's equation becomes:

$$\vec{\Delta} \times \vec{H} = \sigma^* \vec{j} + \vec{j}_0 = (\sigma - i\omega\epsilon_0\epsilon_r)\vec{j} + \vec{j}_0 \quad (2)$$

with the imposed source-current density $\vec{j}_0$.

Hence the electric conductivity generates an in-phase signal while the dielectric permittivity will cause a signal in phase quadrature. For "dielectric spectroscopy" we will measure and characterize this in-phase and quadrature contribution over a wide frequency range.

Water-filled rocks are heterogeneous media that display several competing processes of dielectric polarization. These processes vary in magnitude over the entire frequency range so that at suitably chosen frequency bands the individual contributions dominate and thus can be extracted. For dielectric spectroscopy we start at the upper end of the frequency range, around 0.5-1 GHz. This frequency is used for the dielectric pad-logging tools, such as the EPT and similar tools.

Empirically it has been shown that above ca. 600 MHz the measured complex refractive index, namely the square root of the complex-valued dielectric constant is close to the volumetric average of the complex refractive indices of the constituent materials. This relationship is called the "Comdex Refractive Index Method" (CRIM):

$$\sqrt{\epsilon^*_a} \cong \sum_i \alpha_i \sqrt{\epsilon^*_i} = \\ (1-\Phi)\sqrt{\epsilon_{rock}} + \Phi(1-S_w)\sqrt{\epsilon_{oil,gas}} + \Phi S_w \sqrt{\epsilon^*_{water}} \quad (3)$$

with the relative volume fractions $\alpha_i$, the rock porosity $\Phi$ and the water saturation $S_w$. This formula provides the volumetric contribution of the rock matrix and hydrocarbon content, as well as the volume fraction of water with its conductivity as imaginary part.

To the extent that the dispersion mechanisms spill over other frequencies, the accuracy of (3) will be affected by how close the frequency is to the lower limit of its range, and how conductive the water is. The frequency effect is easy to understand, but the effect of water conductivity will become clear below as we describe the mechanism operating in the next frequency range.

Figure 2:
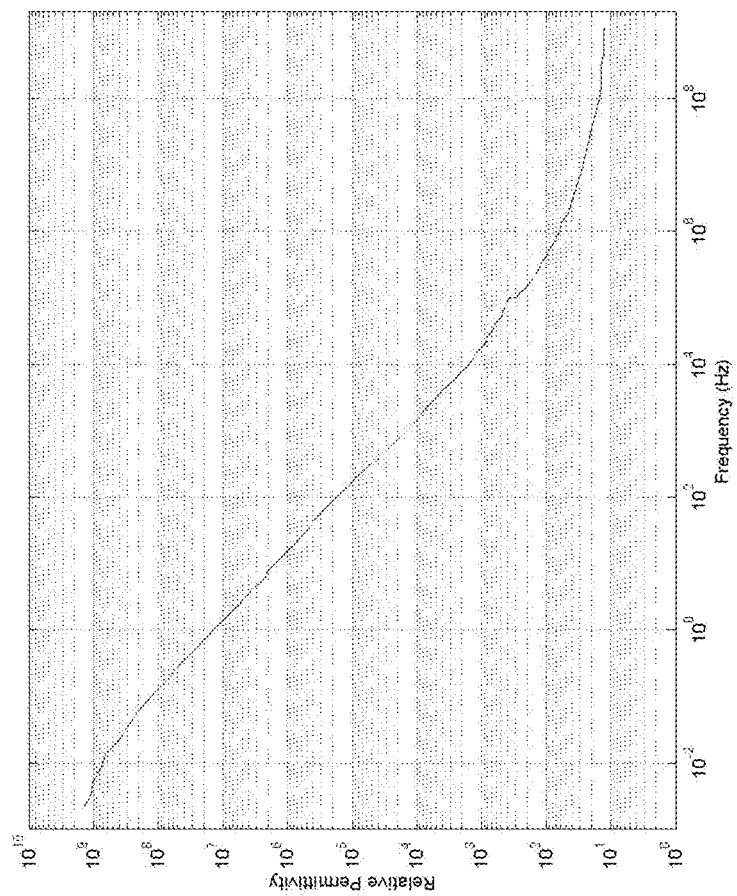
FIG. 2 shows a log-log plot of permittivity as a function of frequency.

FIG. 2 shows a log-log plot of permittivity as a function of frequency. The data shown is for a representative rock sample. Slopes of curves will vary over different frequency ranges for other samples. The frequency range can be from mHz to GHz. This plot clearly shows the permittivity is constant at high frequency ($\epsilon_\infty$=real($\epsilon_a$)). It also shows a 1/f dependence at lower frequencies, a transition zone between these two limits, and anther change of slope at frequencies below 1 Hz. Ignoring the transition below 1 Hz for a moment, FIG. 2 is as a superposition of at least two different curves—a frequency independent line operating at high frequencies and a linear decay operating at lower frequencies. This can be expressed as $$\epsilon_{rock}(f) = \epsilon_1(f) + \epsilon_\infty \quad (4)$$

with:

$$\log(\epsilon_1(f)) = -\beta \log(1 + f/f_0) + \log(\epsilon_0) \quad (5)$$

From FIG. 2, $\epsilon_1$ is much larger than $\epsilon_\infty$ at frequencies below 100 kHz. In (5) $f_0$ is a characteristic frequency that helps render the bracket unit-less and numeral one is introduced to ensure proper behaviour when f approaches zero. $\epsilon_{dc}$ is the permittivity at the lowest frequency where (5) is valid, and is approximated as the dc permittivity which is orders of magnitude larger than $\epsilon_\infty$. $\beta$ is the slope when log of $\epsilon_1$ is plotted vs log $(1+f/f_0)$, this is different from slope of $-1$ in FIG. 2 that is a plot of measured permittivity vs log(f). To obtain an expression for $\beta$, we calculate the slope, S, as, $$S = \frac{\partial \log(\epsilon_1(f))}{\partial \log(f)} = \frac{(f/f_0)}{(1+f/f_0)}(-\beta) \quad (6)$$

which shows S is somewhat frequency dependent. But in the frequency range $f_0 \ll f < 100$ MHz, $S = -1$ leading to $\beta = 1$. This is to say since $\epsilon_\infty$ in this frequency range is much smaller than $\epsilon_1$, the observed slope in FIG. 2 is $\beta$. Using $\beta = 1$ the slope becomes $-\frac{1}{2}$ for $f = f_0$.

Figure 3:
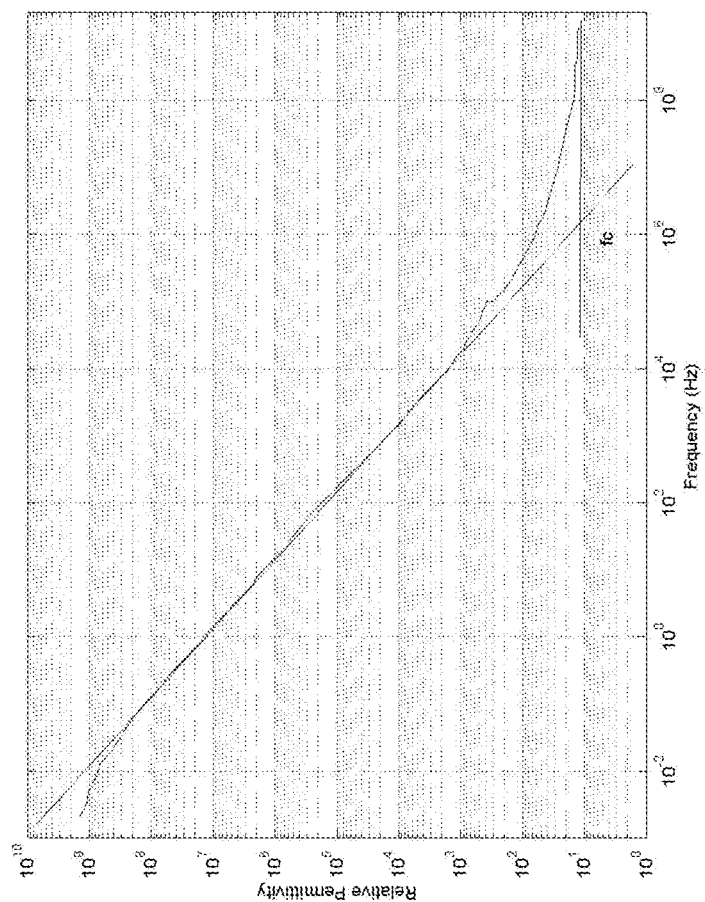
FIG. 3 shows two calculated terms superposed on the plot of FIG. 2.

FIG. 3 shows the two terms of (4) superimposed on the data of FIG. 2. This figure demonstrates how the two terms behave and how the sum of their contributions adds up to represent the measured permittivity data. The two curves intersect at a frequency $f_c$ that is given by, $$-\beta \log(1+f_c/f_0)+\log(\epsilon_{dc})=\log(\epsilon_\infty)$$

FIG. 3 shows this frequency to be in the MHz range so that numeral one can be ignored and the expression simplifies to, $$f_c = f_0\left(\frac{\varepsilon_{dc}}{\varepsilon_\infty}\right) \quad (7)$$

Having measured $f_c$, (7) can be used to calculate $f_0$ which for the data of FIG. 3 is approximately $10^{-2}$ Hz. It is interesting to note that this frequency is in fact approximately the frequency where the permittivity curve starts to bend and level towards what appears to be $\epsilon_0$. While $f_c$ is born purely from (5), it shows some physical significance and may point to the validity of these expressions.

Setting $\beta=1$, there are only three parameters in (4) to be determined. These are $\epsilon_{dc}$, $\epsilon_\infty$, and $f_0$. In addition, a graphical approach similar to what is demonstrated in FIG. 3 can be used to determine $f_c$ and verify the consistency of the fit results. From FIG. 3, there are some preferred frequency ranges that make the fitting step more efficient and reliable. For example, having one measurement point at or above 1 GHz, helps determine $\epsilon_\infty$ and a few points in 0.01-1 MHz range help to determine $\epsilon_1$. High frequency dielectric tools provide data in the 0.1-1 GHz range. The lower frequencies are easier to come by. Resistivity tools such as CDR of Schlumberger make measurements at 2 MHz, which is at about the $f_c$ frequency of FIG. 3. Other tools also measure at 400 kHz and 100 kHz, which are in the linear regimes of FIG. 3. In addition, yet further tools measure at 100, 50, and 2 kHz and the wireline induction tools measure at 10-100 kHz range. These frequencies are best suited to fit the $\epsilon_1$ part. Finally, below ca. 10 kHz some shales exhibit an even larger dielectric effect. Use of wireline laterolog or LWD resistivity at the bit tools with operating frequencies from 35 Hz to 1.5 kHz is well suited to extend the fitting frequency. At these frequencies we observe induced-polarization effects in some shales.

$\epsilon_{dc}$ is obtained from the fit to the data. Combining equations 4 and 5, we get:

$$\log(\epsilon_{rock}-\epsilon_\infty)=-\log(1+f/f_0)+\log(\epsilon_{dc})$$

If the left hand side of this expression is known for at least two frequencies, the two unknowns ($f_0$ and $\epsilon_{dc}$) can be determined using a fitting routine. If it is assumed that $\epsilon_\infty$ is always known from high frequency measurement and $\epsilon_{rock}$ can be obtained from resistivity tool measurements, so that the left hand side is known, and if a number of resistivity measurements at different frequencies are used, the above condition is met. As data for more frequencies are included a better estimate can be made.

Once the fit is made we can calculate $f_c$ using equation 7. $f_c$ can also be determined graphically as is shown in FIG. 3 and compared with the fit results to gain confidence.

A special case is when there are data points available at low enough frequencies where the change of slope from 1 to ½ can be measured. As is shown here, the frequency where slope is ½ is $f_0$. Having measurements at these particular frequencies may or may not be possible. However, if $f_0$ is determined by this method, then $f_c$ can be determined graphically and $\epsilon_{dc}$ can be calculated using equation 7.

Using at least three frequencies from one or more resistivity tool discussed above, it is straightforward to use a fitting or inversion routine to determine the three parameters in (4). Having these parameters one can generate the complete frequency dependence of permittivity and generate the dielectric spectrum of rock samples.

Physically, the slope in the frequency dependence of permittivity is attributed to surface-charge build-up on the rock grains exposed to conductive pore water. Hence the slope is directly related to the shape and surface area or the pore-size distribution as well as the water conductivity. For the same rock grains as the water conductivity increases, this so called geometrical effect to the permittivity dispersion becomes more significant. This is equivalent to $\epsilon_1$ being shifted to higher frequencies as water salinity increases. As a result of this shift in (4), $f_c$ increases implying the product of $\epsilon_{dc}$, and $f_0$ increases as expected from (7).

The slope of a permittivity vs frequency plot is an estimate of the pore-size distribution and thus complements the pore-size distribution measurement from the nuclear-magnetic-resonance logging devices. A thin coat of hydrocarbon on the grain has a different effect on the pore size distribution obtained from permittivity compared with that derived from NMR. For NMR measurements, a layer of oil will only slightly change the diffusion coefficient of the bulk fluid (the effect of oil wettability is most pronounced on the bound fluid rather than on free fluid). For permittivity measurements, however, the effect of an oil layer is the same as increasing the thickness of the insulating layer in the capacitor. This difference can be the basis of a method by which pore size distribution derived from the two physical principles can be compared to determine wettability.

The large dielectric polarization at frequencies below 100 kHz is no longer attributed to geometrical effects. Rather this effect is due to the effect of time varying electric field on the double layer present in clay minerals as shown in FIG. 1. Clay minerals are the components of shale which form thick impermeable layers in the earth structure. In addition, most sandstones are shaly to some extent and there are shale minerals dispersed within the structure of these sandstones. Most often the shale mineral is on the surface of the grain and thus is exposed to the pore water. The so-called double layer effect can lead to extremely large permittivities as seen in FIG. 2. The effect can be further pronounced in rocks with elevated content of pyrite and other electrically conductive micro-nodules. These conductive nodules are isolated and hence build up a macroscopic induced dipole moment in response to an external electric field, thus accounting for the large polarization effects that manifest themselves as very high dielectric permittivities.

Overall, the use of multiple electromagnetic measurements over frequencies from a few Hz to the low GHz range permit to successively quantify and isolate different dielectric phenomena that can be directly tied to different, distinct characteristics in the rock microstructure. This integrated measurement suite and its petrophysical interpretation chain is "dielectric spectroscopy". Determination of dielectric spectroscopy of rocks in situ is not possible with a single logging tool; rather data from multiple tools have to be combined to achieve this goal.

Changes and variations within the scope of the invention will be apparent.

The invention claimed is:

1. A method for determining the frequency-dependent dielectric permittivity spectrum of a rock sample, comprising:
    defining a series of electromagnetic measurement data comprising at least a first measurement at a frequency from which a substantially frequency-independent value of dielectric permittivity $\in_\infty$ can be obtained; and at least second and third measurements at different frequencies from which values for frequency-dependent dielectric permittivity $\in_{rock}(f)$ can be obtained, wherein the first measurement is made at a frequency of $10^8$ Hz or above, and the second and third measurements are made at frequencies of $10^7$ Hz or below; and using the first, second and third measurements to determine the frequency-dependent spectrum of the sample, wherein the frequency-dependent part of the spectrum obeys the relationship $\in_{rock}(f) = \in_1(f) + \in_\infty$ wherein $\in_1(f)$ defines the frequency-dependent part of a measured value of dielectric permittivity, the method further comprising:

determining the dc permittivity $\in_{dc}$;

determining the characteristic frequency $f_0$, the lowest frequency for which the relationship $\log(\in_1(f)) = -\beta \log(1+f/f_0) + \log(\in_{dc})$ holds substantially true; and determining the slope of the frequency dependent part of the spectrum between $f_0$ and the frequency $f_c$ at which the spectrum becomes substantially frequency independent.

2. A method as claimed in claim 1, further comprising determining $\in_{dc}$ and $f_0$ by providing measurements of $\in_{rock}$ (f) for at least two frequencies and applying a fitting routine to the relationship $\log(\in_{rock} - \in_\infty) + -\log(1+f/f_0) + \log(\in_{dc})$.

3. A method as claimed in claim 1, wherein $f_c$ is determined from the relationship $f_c = f_0(\in_{dc}/\in_\infty)$.

4. A method as claimed in claim 1, wherein the slope is the slope of the plot of $\log \in_1$ vs $\log(1+f/f_0)$.

5. A method as claimed in claim 4, further comprising determining $f_c$ from the plot.

6. A method as claimed in claim 1, further comprising using the slope to estimate the pore size distribution of the rock.

7. A method as claimed in claim 1, further comprising using the value of $f_c$ to estimate the salinity of the pore fluids in the rock.

8. A method as claimed in claim 1, further comprising making a series of electromagnetic measurements in a borehole extending through the rock sample and using the measurement to define the data series.

9. A method as claimed in claim 8, wherein the first measurement is obtained in a separate operation from the second and third measurements.

10. A method as claimed in claim 1, wherein the measurements are a combination of wireline and/or LWD measurements.

* * * * *